(12) United States Patent
Palmieri

(10) Patent No.: US 8,956,325 B2
(45) Date of Patent: Feb. 17, 2015

(54) PIEZOELECTRIC MICROFLUIDIC PUMPING DEVICE AND METHOD FOR USING THE SAME

(75) Inventor: Michele Palmieri, Corvallis, OR (US)

(73) Assignee: STMicroelectronics, Inc., Coppell, TX (US)

( * ) Notice: Subject to any disclaimer, the term of this patent is extended or adjusted under 35 U.S.C. 154(b) by 0 days.

(21) Appl. No.: 13/313,443

(22) Filed: Dec. 7, 2011

(65) Prior Publication Data

US 2013/0150790 A1 Jun. 13, 2013

(51) Int. Cl.
*A61M 1/00* (2006.01)
*F04B 17/00* (2006.01)
*A61M 5/142* (2006.01)

(52) U.S. Cl.
CPC ....... *A61M 5/142* (2013.01); *A61M 2205/0244* (2013.01)
USPC ........................................ 604/153; 417/413.3

(58) Field of Classification Search
CPC ...................... A61M 5/142; A61M 2205/0244
USPC ........ 604/153, 891.1; 251/129.01; 417/413.2; 137/831
See application file for complete search history.

(56) References Cited

U.S. PATENT DOCUMENTS

| | | | |
|---|---|---|---|
| 5,588,466 A * | 12/1996 | Benz et al. ................. | 137/831 |
| 6,294,860 B1 | 9/2001 | Shimada et al. ............ | 310/328 |
| 6,533,400 B1 * | 3/2003 | Kudo et al. ................. | 347/63 |
| 6,589,198 B1 * | 7/2003 | Soltanpour et al. ......... | 604/9 |
| 6,673,593 B2 | 1/2004 | Mastromatteo et al. ... | 435/283.1 |
| 6,693,039 B2 | 2/2004 | Erratico et al. ............. | 438/700 |
| 6,770,471 B2 | 8/2004 | Barlocchi et al. .......... | 435/287.2 |
| 7,618,391 B2 * | 11/2009 | Madsen et al. ............. | 604/9 |
| 7,678,600 B2 | 3/2010 | Villa et al. ................. | 438/48 |
| 7,705,416 B2 | 4/2010 | Barlocchi et al. .......... | 257/510 |
| 7,754,578 B2 | 7/2010 | Villa et al. ................. | 438/422 |
| 7,811,848 B2 | 10/2010 | Barlocchi et al. .......... | 438/52 |
| 8,231,608 B2 * | 7/2012 | Pang et al. ................. | 604/891.1 |
| 2009/0010780 A1 * | 1/2009 | Kamitani et al. .......... | 417/413.2 |
| 2009/0112155 A1 * | 4/2009 | Zhao et al. ................. | 604/67 |
| 2009/0188576 A1 * | 7/2009 | Kang et al. ................. | 137/831 |
| 2010/0021322 A1 * | 1/2010 | Kitahara et al. ........... | 417/413.2 |
| 2011/0103980 A1 * | 5/2011 | Mandica ..................... | 417/413.2 |

FOREIGN PATENT DOCUMENTS

| | | | |
|---|---|---|---|
| JP | 2003-1333604 A | 5/2003 | |
| JP | 2010-287268 A | 12/2010 | |

OTHER PUBLICATIONS

Farrens et al., "Polymers for Permanent Wafer Bonding," Sensors Expo, Chicago, IL, Jun. 9, 2008, 2 pages.
Kräuter et al., "Room Temperature Silicon Wafer Bonding with Ultra-Thin Polymer Films," *Adv. Mater.*, vol. 9(5):417-420, 1997.
Palmieri, "Microfluidic Jetting Device With Piezoelectric Actuator and Method for Making the Same," U.S. Appl. No. 13/294,956, filed Nov. 11, 2011, 40 pages.

* cited by examiner

*Primary Examiner* — Theodore Stigell
*Assistant Examiner* — Benjamin Koo
(74) *Attorney, Agent, or Firm* — Seed IP Law Group PLLC

(57) ABSTRACT

Disclosed herein is a microfluidic pumping device having a piezoelectric member positioned above a displaceable membrane. A voltage is applied across the piezoelectric member causing the piezoelectric member to displace the membrane. Displacement of the membrane increases and decreases pressure in a cavity that is below the membrane. The increases and decreases in pressure actuate cantilevered check valve members to facilitate unidirectional liquid flow through the pumping device.

13 Claims, 5 Drawing Sheets

PIEZOELECTRIC MICROFLUIDIC PUMPING DEVICE AND METHOD FOR USING THE SAME

BACKGROUND

1. Technical Field

The present disclosure generally relates to a piezoelectric microfluidic pumping device.

2. Description of the Related Art

Piezoelectric materials are useful for actuating electromechanical devices. Piezoelectric materials are those that exhibit both a piezoelectric effect and a reverse piezoelectric effect. The piezoelectric effect is the generation of a voltage across opposite faces of a piezoelectric material in response to applying pressure to the piezoelectric material. The reverse piezoelectric effect is the contraction, expansion, or otherwise deformation of a piezoelectric material in response to applying an electric field across the piezoelectric material. Some approaches to pumping liquid utilize the reverse piezoelectric effect for actuation.

U.S. Pat. No. 6,294,860 (hereinafter '860 patent) describes an ink jet recording device equipped with a piezoelectric film element. The recording device includes a vibrating plate with a piezoelectric film placed over an ink reservoir formed in a first substrate. The vibrating plate creates pressure within the ink reservoir causing ink to eject from the ink reservoir. The ink reservoir is formed by entirely removing a portion of the first substrate located directly beneath the piezoelectric film. Ink is ejected from the ink reservoir through an ink jetting nozzle formed in a second substrate that is bonded to a lower surface of the first substrate so that the nozzle jets ink in a direction that is away from the piezoelectric film.

Japanese publication JP2003133604 describes an ink jet recording device that is similar to '860 patent with the exception that a nozzle is formed in a plate that is thinner than the second substrate of the '860 patent, however, similar to the '860 patent the thin plate is bonded to the bottom of the first substrate.

The existing approaches appear to be limited to pumping liquid in a direction that is away from the piezoelectric element out of a reservoir that extends completely through a substrate that is below the piezoelectric element.

BRIEF SUMMARY

Various embodiments of the invention are directed towards a piezoelectric microfluidic pumping device having a cavity formed in a lower substrate. The pumping device includes an inlet valve member and an outlet valve member suspended above the cavity. The valve members flexibly swing in and out of the cavity in response to the displacement of a piezoelectrically displaceable membrane that is positioned above the cavity. When the displaceable membrane is displaced toward the cavity, the inlet valve member seats against an upper substrate to a shut position to inhibit back-flow of liquid from the cavity back into an inlet chamber, and the outlet valve member flexibly swings towards the upper substrate to an open position to facilitate liquid flow from the cavity into an outlet chamber. When the displaceable membrane is displaced away from the cavity, the inlet valve member flexibly swings into the cavity to facilitate liquid flow from the inlet chamber into the cavity, and the outlet valve member flexibly swings towards the cavity and seats against the lower substrate to inhibit liquid back-flow from the outlet chamber into the cavity.

According to one embodiment, the pumping device is part of a cutaneous drug delivery device and moves liquid drug agents from a reservoir to a drug diffusible membrane for absorption through the skin of a patient.

Advantageously, the inlet valve member and the outlet valve member are respectively part of an inlet check valve and an outlet check valve which enable minutely controllable amounts of liquid to flow unidirectionally. Additionally, the pumping device is advantageously formed using standard semiconductor processes, thus allowing the pumping device to be economically manufactured individually or as part of an integrated circuit, according to one embodiment of the invention.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles, and some of the elements are enlarged and positioned to improve understanding of the inventive features

DETAILED DESCRIPTION

In the description provided herewith, certain specific details are set forth in order to provide a thorough understanding of various disclosed embodiments. However, one skilled in the relevant art will recognize that embodiments may be practiced without one or more of these specific details, or with other methods, components, etc. In some instances, well-known structures or processes associated with fabrication of MEMS have not been shown or described in detail to avoid unnecessarily obscuring descriptions of the inventive embodiments.

Unless the context requires otherwise, throughout the specification and claims that follow, the words "comprise" and "include" and variations thereof, such as "comprises," "comprising," and "including," are to be construed in an open, inclusive sense, that is, as meaning "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment.

Furthermore, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

As used in the specification and appended claims, the use of "correspond," "corresponds," and "corresponding" is intended to describe a ratio of or a similarity between referenced objects. The use of "correspond" or one of its forms should not be construed to mean the exact shape or size.

Figure 1:
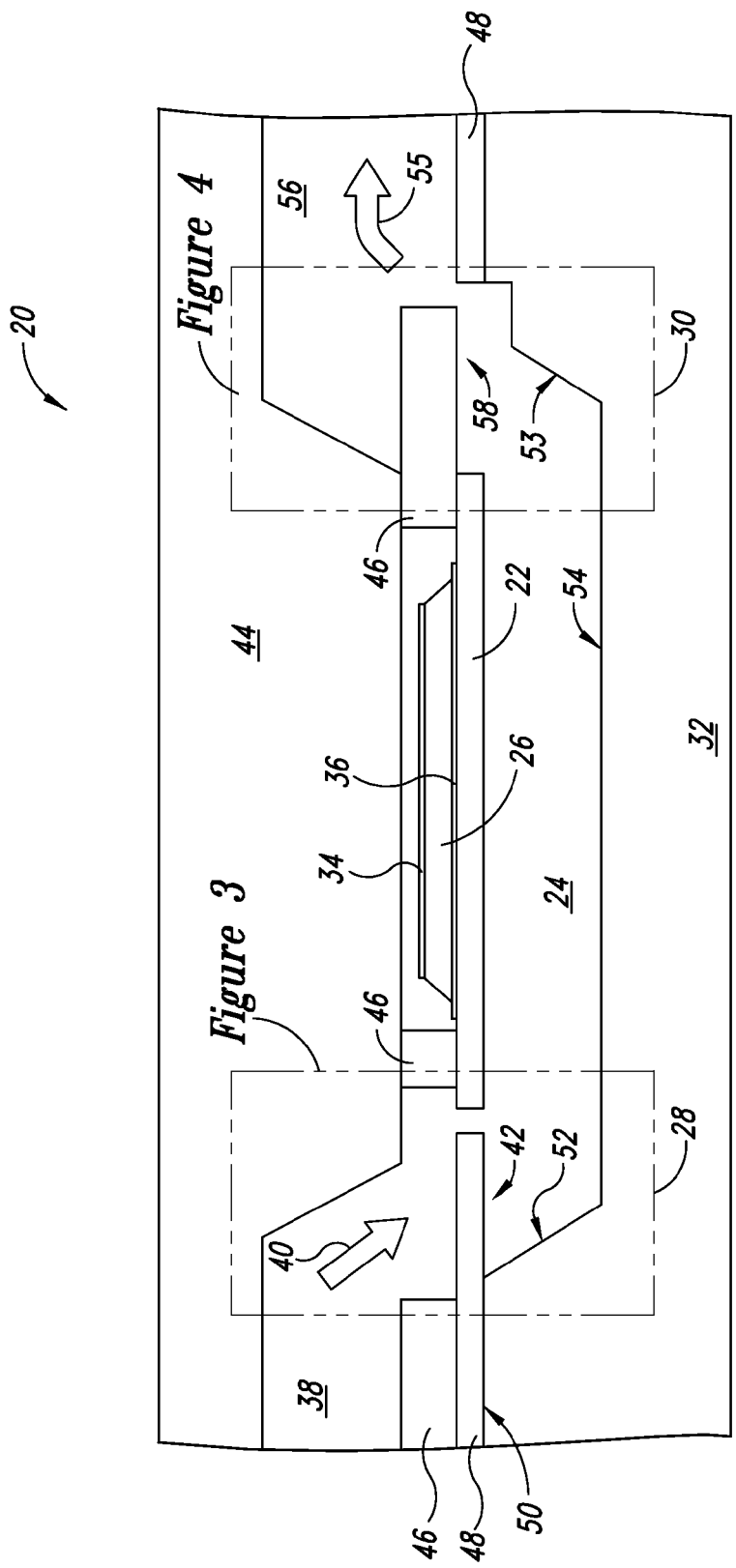
FIG. 1 is a schematic cross-sectional view of a pumping device, according to an embodiment of the invention.

FIG. 1 is a schematic cross-section illustrating a pumping device 20, according to one embodiment of the invention. The pumping device 20 includes a membrane 22, a cavity 24, a piezoelectric element 26, an inlet valve 28, and an outlet valve 30.

The membrane 22 is positioned above the cavity 24 to at least partially enclose the cavity, according to one embodiment of the invention. The membrane 22 may be formed using one of various techniques described in the related application, having USPTO application Ser. No. 13/294,956, invented by Michele Palmieri, filed on Nov. 11, 2011, titled "MICROFLUIDIC JETTING DEVICE WITH PIEZOELECTRIC ACTUATOR AND METHOD FOR MAKING THE SAME."

Following is a summary of various ways to construct the membrane 22. According to one embodiment, the membrane 22 is composed of a plurality of fingers of a first dielectric surrounded by a second dielectric. The first dielectric is an oxide layer, and the second dielectric is a nitride layer. The membrane 22 may also include a layer of polysilicon deposited above the first and second dielectric layers. Alternatively, the membrane 22 includes a plurality of fingers of monosilicon that extend across a length or width of the cavity 24 and that are separated from one another by a plurality of spaces. The plurality of fingers are laterally joined together by depositing one or more layers around the plurality of fingers or by growing epitaxial silicon, or pseudo-epitaxial silicon, around the plurality of fingers. The membrane 22 has a thickness ranging from hundreds of nanometers to tens of microns, and the membrane 22 is optionally polished to achieve a smooth surface prior to the deposition of subsequent layers.

The membrane 22 is configured to be flexibly displaced in order to draw liquid into the cavity 24 and to expel liquid from the cavity 24. Displacing the membrane 22 into the cavity 24 compresses the liquid contained in the cavity 24 and increases pressure therein. This increased pressure is a force that expels liquid from the cavity 24 through the outlet valve 30 along a path indicated by arrow 55, as will be discussed in more detail below. Displacing or deflecting the membrane 22 away from the cavity 24 decreases pressure within the cavity 24. This decreased pressure results in a suction of additional liquid into the cavity 24 through the inlet valve 28 along a path indicated by arrow 40.

The cavity 24 is opened during one or more of the processes used to form the membrane 22, according to one embodiment of the invention. The cavity 24 is opened in a substrate 32 using one of a variety of techniques described in the related application Ser. No. 13/294,956. For example, a plurality of shallow channels are created in the membrane 22 that extend down into the substrate 32, and a subsequent isotropic etch is applied to the plurality of shallow channels. The isotropic etch removes a quantity of the substrate 32 that is below the plurality of shallow channels until the cavity 24 is opened below the membrane 22. Optionally, the channels are anisotropically etched into the substrate 32 to a depth that is several times the thickness of the membrane 22, and an isotropic etch is subsequently performed to remove substantially all of the portions of the substrate 32 that are between the plurality of channels and below the membrane 22. After creating the cavity, the channels in the membrane 22 are filled with one or more dielectrics, monocrystalline silicon, or polycrystalline silicon, as described above. The cavity 24 has a width ranging between tens of micrometers to hundreds of micrometers as measured between the two walls 52 and 53 of the cavity 24, according to one embodiment. The cavity 24 has a length ranging between hundreds of micrometers to tens of millimeters, according to one embodiment. The length direction is into the page on FIG. 1 and part of the length can be seen in FIG. 3B. The cavity 24 has a depth extending from the bottom wall of membrane 22 to a floor 54 of the cavity that ranges between tens of micrometers to hundreds of micrometers, according to one embodiment.

There are a large number of different techniques that can be used to form cavity 24 with the membrane 22 overlying a substantial portion of the cavity and any of these may be used as well.

The piezoelectric element 26 is positioned above the membrane 22 and is configured to displace the membrane 22 through a reverse piezoelectric effect, according to one embodiment. An example of a piezoelectric material is PZT (lead zirconate titante). PZT is a ceramic perovskite material. Other examples of piezoelectric materials include crystals such as gallium orthophosphate and ceramics such as barium titanate, lead titanate, and lithium niobate. According to one embodiment, the piezoelectric element 26 is PZT. According to other embodiments, the piezoelectric element 26 is one of gallium orthophosphate, barium titanate, lead titanate, lithium niobate, and the like. The piezoelectric element 26 is deposited with a sol-gel spin coat, sputtering, CVD, or the like. The piezoelectric element 26 has a thickness ranging from hundreds of nanometers to tens of micrometers, according to one embodiment. After the deposition of the piezoelectric element 26, thermal treatments are applied to the microfluidic pumping device 20 to produce a perovskite ceramic characteristic of the piezoelectric element 26 to enhance the piezoelectric effects of the piezoelectric element 26.

The piezoelectric element 26 is electrically stimulated with an upper electrode 34 and a lower electrode 36 which are disposed above and below the piezoelectric element 26, respectively. The upper electrode 34 and the lower electrode 36 are deposited as thin film layers, according to one embodiment. After the membrane 22 has been formed, an electrically conductive layer is formed thereon. It is masked and etched using resist to provide a desired end shape for lower electrode 36. The lower electrode 36 is deposited using CVD and is a silicide layer that is titanium silicide, tungsten silicide, or the like, according to one embodiment. While the use of a silicide is one type of acceptable conductor for electrode 36, it is within the scope of embodiments of the invention to use other thin-film conductive layers, such as platinum, for both the upper electrode 34 and the lower electrode 36. The upper electrode 34 is deposited after the deposition of the piezoelectric element 26, using processes similar to those used to form the lower electrode 36.

The upper and lower electrodes 34, 36 are configured to receive electrical signals and generate an electric field $E_z$ across the piezoelectric element 26. The strength of the electric field $E_z$ applied to the piezoelectric element 26 is directly proportional to the voltage V of the signal applied and indirectly proportional to the thickness d of the piezoelectric element 26. The applied electric field is expressed as $E_z=V/d$, according to one embodiment of the invention.

An inlet chamber 38 is selectively communicatively coupled and decoupled from the cavity 24 via the inlet valve 28 to permit liquid to unidirectionally flow into the cavity 24 as indicated by the arrow 40. The inlet chamber 38 is a cavity that includes upper boundaries defined by an upper layer 44 and lower boundaries defined by the substrate 32 and layer 46 (see FIG. 5). The upper layer 44 is positioned above the substrate 32 as part of a wafer on wafer process, according to one embodiment of the invention. In the wafer-on-wafer process, the upper layer 44 is a lid that is formed from a separate silicon wafer that is placed over the top of the substrate 32 and sealed in place. This is explained in more detail with respect to FIG. 5. The upper layer 44 may also be a layer that is chemically or physically deposited above the substrate 32 and may also be provided by a different technique than a wafer-on-wafer process. Accordingly, the dimensions of the inlet chamber 38 are formed prior to positioning the upper layer 44 above the substrate 32. Alternatively, the upper layer 44 is polysilicon, and the inlet chamber 38 is created in the upper layer 44 after the upper layer 44 is deposited above the substrate 32.

A layer 46 adheres the upper layer 44 to the substrate 32, according to one embodiment of the invention. The layer 46, which is a polymeric layer, can be a laminated dry film, negative photoresist, polyimide, or epoxy polymer, such as polymethylmethacrylate (PMMA) or trimethylsilylcellulose (TMSC), to name a few. The layer 46 can be spin-coated onto an intermediate wafer and transferred onto the substrate 32 or upper layer 44 using a method similar to an ordinary stamp. Thereafter, the upper layer 44 may be bonded to the substrate 32 by joining the upper layer 44 and the substrate 32 with a predetermined amount of pressure. The bond between the substrate 32 and the upper layer 44 may be subsequently strengthened by annealing the bond with a heat treatment at, for example, 50-200° C. Advantageously, bonding a substrate 32 with upper layer 44 creates a moisture resistant seal to reinforce the unidirectional flow of liquid through the pumping device 20.

The layer 46 is coupled to the substrate 32 through a layer 48. The layer 48 may include one or more dielectrics such as silicon oxide, silicon dioxide, silicon nitride, or the like that are grown or deposited above the substrate 32 using semiconductor processes that are well-known in the art.

The inlet valve 28 is a check valve that selectively communicatively couples and decouples the inlet chamber 38 to the cavity 24. Walls of the inlet valve 28 include portions of the inlet chamber 38, the layer 46, the membrane 22, and the cavity 24, as depicted in FIG. 1.

The inlet valve 28 includes an inlet valve member 42 configured as a gate of the inlet valve 28, according to one embodiment of the invention. The inlet valve member 42 is a cantilever that extends from an upper surface 50 of the substrate 32 to cantileverly swing into and away from the cavity 24, as will be shown in more detail in FIG. 3A. The inlet valve member 42 is formed at the same time as the membrane 22 using the same semiconductor processes. Accordingly, the inlet valve member 42 is a composite of a plurality of dielectrics, a composite of monocrystalline silicon and at least one dielectric, or substantially monocrystalline, according to various embodiments of the invention. Subsequent to the formation of the membrane 22 a portion of it is etched completely away from membrane 22 to form the inlet valve member 42. The inlet valve member 42 is released from the membrane 22 to suspend above the cavity 24 and to cantileverly swing into and away from the cavity 24 to open and shut the valve 28, respectively.

The inlet valve member 42 may be created using techniques that differ from the ones described above. For example, the inlet valve member 42 may be an integral part of and extend from of the membrane 22, rather than from the layer 48, and be separated from the layer 48 and suspended over the substrate 32. Alternatively, the inlet valve member 42 is formed at the same time as and includes the same composition as the layer 48, which is different from the membrane 22. The inlet valve member 42 may also formed from the layer 46, which is above the substrate 32 and the layer 48, as explained later herein.

An outlet chamber 56 is selectively communicatively coupled and decoupled from the cavity 24 via the outlet valve 30 to permit liquid to flow from the cavity 24 to the outlet chamber 56, as indicated by the arrow 55. The outlet chamber 56 is a cavity that includes upper boundaries defined by the upper layer 44 and lower boundaries defined by the substrate 32. The dimensions of the outlet chamber 56 are formed prior to positioning the upper layer 44 above the substrate 32, or the dimensions of the outlet chamber 56 are formed during the deposition of the upper layer 44, according to various embodiments of the invention.

The outlet valve 30 is a check valve that selectively communicatively couples and decouples the cavity 24 to the outlet chamber 56. Walls of the outlet valve 30 include portions of the cavity 24, the layer 46, the membrane 22, and the outlet chamber 56, as illustrated in FIG. 1.

The outlet valve 30 includes an outlet valve member 58 configured as a gate of the outlet valve 30, according to one embodiment of the invention. The outlet valve member 58 is a cantilever that extends from between the membrane 22 and the upper layer 44 to cantileverly swing into and away from at least part of the cavity 24, as will be shown in more detail in FIG. 4A. The outlet valve member 58 is an extension of the layer 46. As discussed above, the layer 46 is a polymeric layer can be a laminated dry film, negative photoresist, polyimide, or epoxy polymer that is deposited onto the upper layer 44 or the substrate 32.

The outlet valve member 58 may be formed using a variety of alternative techniques. For example, the outlet valve member 58 may be formed as an extension of the membrane 22 to suspend over the cavity 24 directly from the membrane 22. Accordingly, the outlet valve member 58 can be a composite of a plurality of dielectrics, a composite of monocrystalline silicon and at least one dielectric, or substantially monocrystalline. As another example, the outlet valve member 58 may be formed to extend from the layer 48 and include the same composition as the layer 48. Alternatively, the outlet valve member 58 may be formed to extend from the layer 48 and include a similar cross-sectional composition as the membrane 22. As yet another alternative, the outlet valve member 58 is formed from the layer 46, is decoupled from the membrane 22, and is anchored directly above the layer 48 and the substrate 32 to cantileverly swing into and out of the cavity 24.

Figure 2:
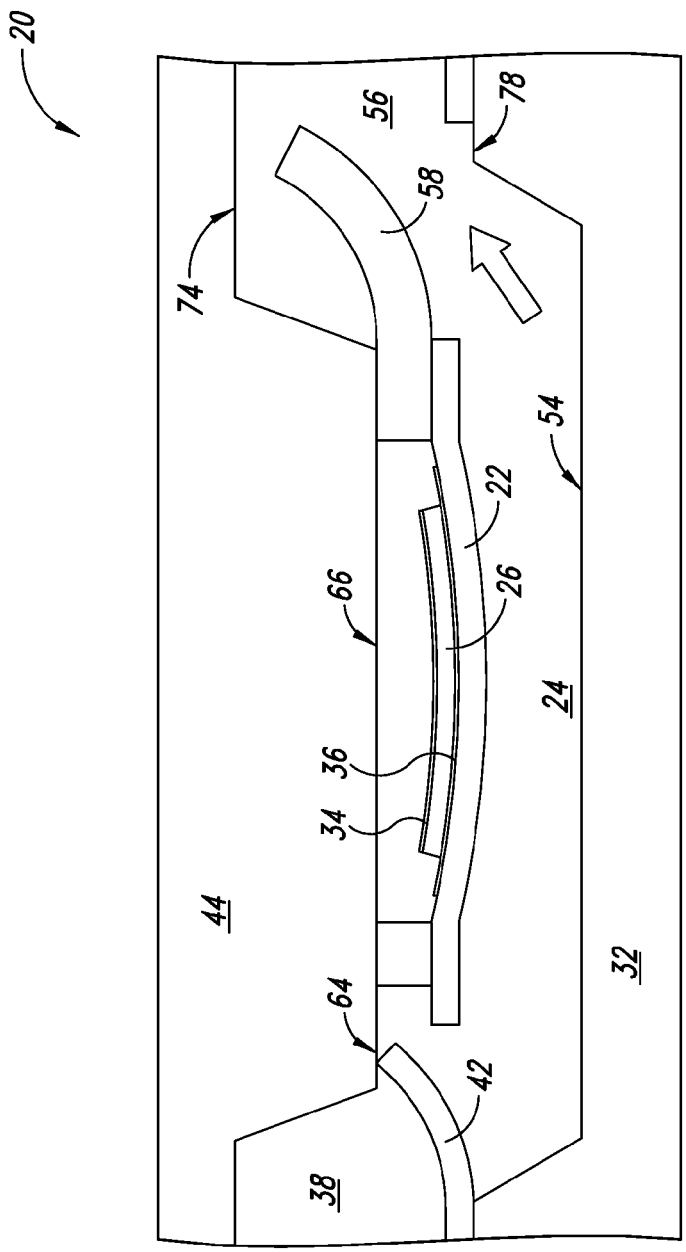
FIG. 2 is a schematic cross-sectional view illustrating the actuation of the pumping device of FIG. 1, according to an embodiment of the invention.

FIG. 2 illustrates a cross-sectional view of the operation of the pumping device 20, according to one embodiment of the invention. In response to a positive electric field applied across the piezoelectric element 26 from the upper electrode 34 to the lower electrode 36, the membrane 22 is deflected towards the cavity 24 to apply pressure to liquid within the cavity 24. As a result of increased pressure on liquid in the cavity 24, the inlet valve member 42 displaces towards, or seats against, the ceiling 64 in the shut position. Concurrently, the outlet valve member 58 displaces towards the ceiling 74 in the open position. In the shut position, the inlet valve member 42 inhibits flow from the cavity 24 into the inlet chamber 38. In the open position, the outlet valve member 58 facilitates flow of liquid from the cavity 24 to the outlet chamber 56.

By removing and reversing to zero the applied positive electric field across the piezoelectric element 26 from the upper electrode 34 to the lower electrode 36, the membrane 22 will move back in the direction of the ceiling 66 and return to its rest position, thus decreasing the pressure in the cavity 24. In response, the inlet valve member 42 displaces towards the floor 54 of the cavity 24 in the open position to facilitate flow into the cavity from the inlet chamber 38. Concurrently, the outlet valve member 58 displaces towards or seats against the step 78 of the cavity 24 in the closed position to inhibit flow into the cavity 24 from the outlet chamber 56.

Figure 3A:
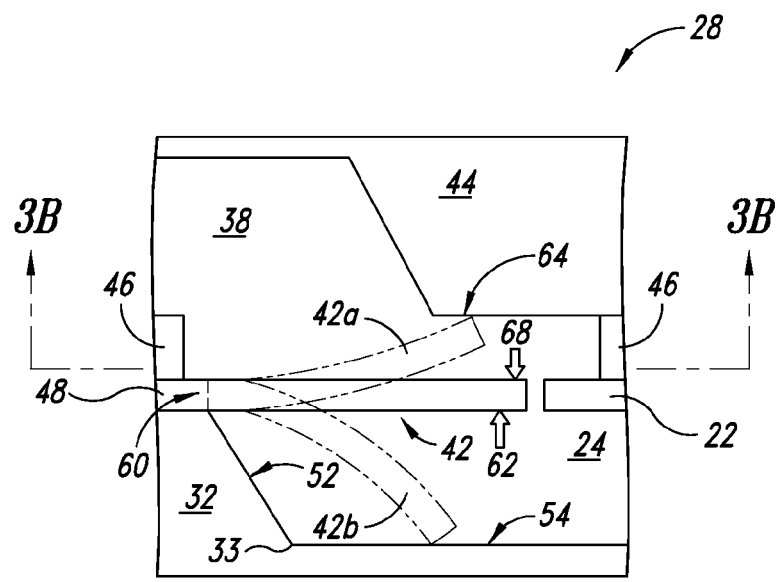
FIG. 3A is a schematic cross-sectional view of an inlet valve of the pumping device of FIG. 1, according to an embodiment of the invention.
Figure 3B:
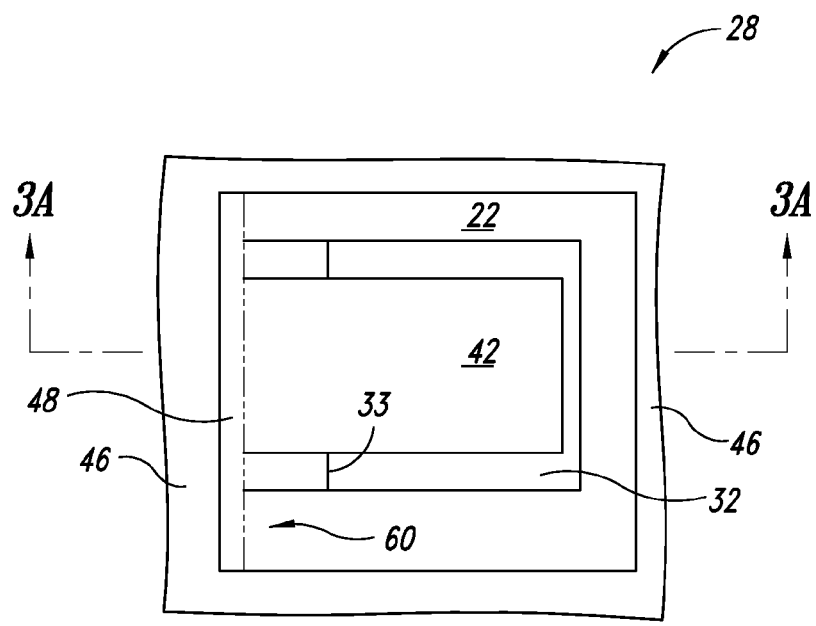
FIG. 3B is a top plan view of the cross-sectional view of FIG. 2A, according to an embodiment of the invention.

FIG. 3A is a schematic cross-sectional view of FIG. 3B at lines 3A-3A and illustrates the operation of the inlet check valve 28, according to one embodiment of the invention. As discussed above, the inlet valve member 42 is a cantilever that flexibly swings between the cavity 24 and the inlet chamber 38 in response to respective displacements of the membrane 22 by the piezoelectric element 26. The inlet valve member 42 pivots along a boundary line 60 that distinguishes the inlet valve member 42 from the layer 48.

The inlet valve member 42 can be placed in three different positions, a resting or neutral position (shown as 42), a shut position 42a, and an open position 42b.

Displacing the membrane 22 into the cavity 24 increases pressure on the liquid in the cavity 24, resulting in an upward force 62 on the inlet valve member 42. The upward force 62 displaces the inlet valve member 42 from a resting or neutral position to the shut position 42a. According to one embodiment, the shut position 42a includes the inlet valve member 42 being seated against a ceiling 64 that is defined by the upper layer 44. While in the shut position 42a, the inlet valve member 42 substantially inhibits back-flow of liquid from the cavity 24 to the inlet chamber 38. According to one embodiment, seating the inlet valve member 42 against the ceiling 64 in the shut position 42a completely stops liquid from flowing into the inlet chamber 38 from the cavity 24. The inlet valve member 42 is configured to selectively communicatively couple and decouple the cavity 24 from the inlet chamber 38.

Displacing the membrane 22 away from the cavity 24 and back to its rest position lowers pressure in the cavity 24, resulting in a suction or a downward force 68 on the inlet valve member 42. The downward force 68 displaces the inlet valve member 42 from a resting or neutral position to the open position 42b. According to one embodiment, the open position 42b includes the inlet valve member 42 being pressed against the floor 56 (shown in FIG. 1) that is defined by the substrate 32. While in the open position 42b, the inlet valve member 42 enables free flow of liquid from the inlet chamber 38 to the cavity 24. Thus, the inlet valve member 42 is configured to selectively communicatively couple and decouple the inlet chamber 38 to the cavity 24.

FIG. 3B is a top plan view of FIG. 3A at lines 3B-3B, according to one embodiment of the invention. The inlet valve member 42 has been released from the membrane 22 so the inlet valve member 42 is separated from the membrane 22 by a gap. Looking through the gap that is between the inlet valve member 42 and the membrane 22, the substrate 32 and a bottom corner 33 of the cavity 24 can both be seen. According to one embodiment, the layer 46 surrounds the inlet valve member 42. The distance of the gap between valve member 42 and surrounding membrane 22 is selected to be sufficiently large permit movement of the valve 42, but not so large as to permit fluid to pass through when valve 42 is closed. Thus, the walls of 22 or the layer 46 will be somewhat closer to the valve 42 at the locations above it so that when the valve is in the closed position, 42a, there is little to no space and no fluid can pass there through. It is shown somewhat enlarged for ease in viewing in FIG. 3B, and in many embodiments, the gap all sides of valve 42 will be quite narrow and uniform when the valve is in the neutral position. The distance of the gap between the valve 42 and layer 22 can be selected based on the surface tension and viscosity of the fluid being pumped so that it does not pass through the gap when the valve 42 is in the neutral position or the closed position.

Figure 4A:
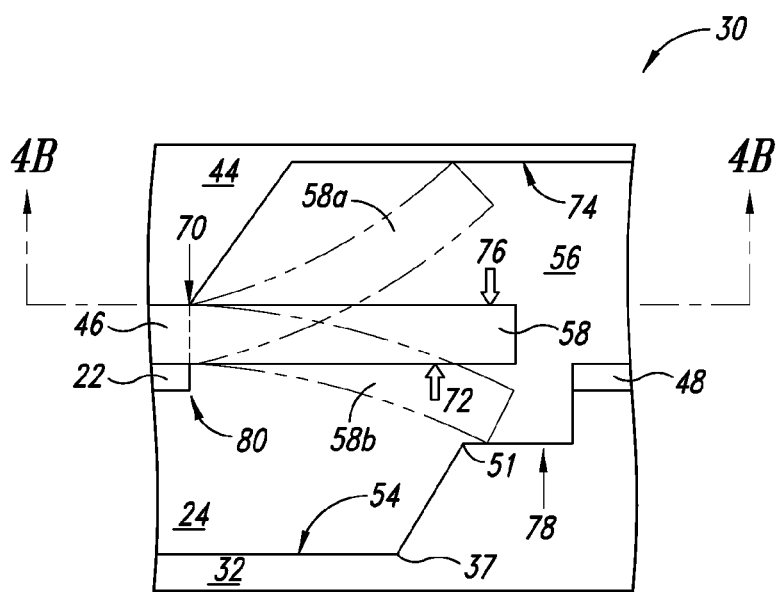
FIG. 4A is a schematic cross-sectional view of an outlet valve of the pumping device of FIG. 1, according to an embodiment of the invention.
Figure 4B:
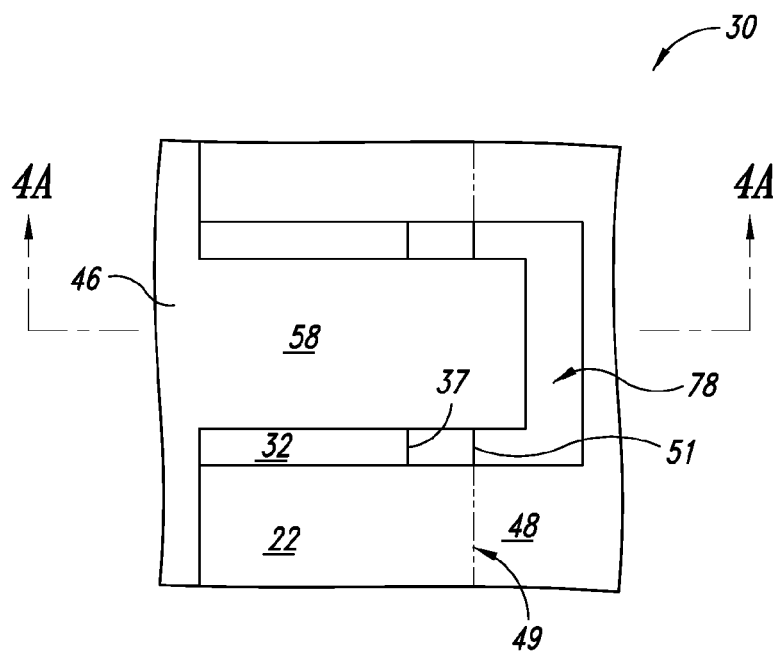
FIG. 4B is a top plan view of the cross-sectional view of FIG. 3A, according to an embodiment of the invention.

FIG. 4A is a schematic cross-sectional view of FIG. 4B at lines 4A-4A and illustrates the operation of the outlet check valve 30, according to one embodiment of the invention. As discussed above, the outlet valve member 58 is a cantilever that flexibly swings between the outlet chamber 56 and the cavity 24 in response to respective displacements of the membrane 22 by the piezoelectric element 26. The outlet valve member 58 pivots along a boundary line 70 which indicates a boundary of the outlet chamber 56 that is above the outlet valve member 58.

The outlet valve member 58 can be placed in three different positions, a resting or neutral position (shown as 58), an open position 58a, and a shut position 58b.

Displacing the membrane 22 into the cavity 24 increases pressure on the liquid in the cavity 24, resulting in an upward force 72 on the outlet valve member 58. The upward force 72 displaces the outlet valve member 58 from a resting or neutral position to the open position 58a. According to one embodiment, the open position 58a includes the outlet valve member 58 being seated against a ceiling 74 that is defined by the upper layer 44 within the outlet chamber 56. While in the open position 58a, the outlet valve member 58 substantially freely permits the flow of liquid from the cavity 24 to outlet chamber 56. Thus, the outlet valve member 58 is configured to selectively communicatively couple and decouple the cavity 24 to the outlet chamber 56.

Displacing the membrane 22 away from the cavity 24 and back to its rest position, lowers pressure in the cavity 24, resulting in a suction or a downward force 76 on the outlet valve member 58. The downward force 76 displaces the outlet valve member 58 from a resting or neutral position to the shut position 58b. According to one embodiment, the shut position 58b includes the outlet valve member 58 being pressed against a step 78 of the cavity 24 that is defined by the substrate 32, the substrate having an upper corner 51 and a bottom corner 37. While in the shut position 58b, the outlet valve member 58 substantially inhibits the flow of liquid from the outlet chamber 56 into the cavity 24. Alternatively, seating the outlet valve member 58 in the shut position 58b completely stops liquid from flowing into the cavity 24 from the outlet chamber 56. Thus, the outlet valve member 58 is configured to selectively communicatively couple and decouple the cavity 24 from the outlet chamber 56.

FIG. 4B is a top plan view of FIG. 4A at lines 4B-4B, according to one embodiment of the invention. The outlet valve member 58 extends from the layer 46 from the left to the right. FIG. 4B also shows that the opening is formed through the membrane 22 and the layer 48 in order to allow the outlet valve member 58 to swing freely into the cavity 24. The substrate 32, the bottom corner 37 and the upper corner 51 can be seen through the opening formed in the membrane 22 and the layer 48 under the outlet valve member 58. A line 49 distinguishes the layer 48 and the membrane 22 according to embodiments where the layer 48 has a composition that is different a composition of the membrane 22. Similar to the gap between the valve 42 and the member 22, the distance of the gap between valve member 58 and surrounding membrane 22 is selected to be sufficiently large permit movement of the valve 58, but not so large as to permit fluid to pass through when valve 58 is closed. Thus, the walls of 22 or the layer 46 will be somewhat closer to the valve 58 at the locations below it so that when the valve is in the closed position, 58b, there is little to no space and no fluid can pass there through. It is shown somewhat enlarged for ease in viewing in FIG. 4B, and in many embodiments, the gap all sides of valve 58 will be quite narrow and uniform when the valve is in the neutral position. The distance of the gap between the valve 58 and layer 22 can be selected based on the surface tension and viscosity of the fluid being pumped so that it does not pass through the gap when the valve 58 is in the neutral position or the closed position.

Operating as part of a drug delivery device or system, the pumping device 20 provides several advantages. In particular, the pumping device 20 delivers controllable and minute quantities of liquid based on the size of the cavity 24.

The size of the cavity 24, at least partially, determines the volume of liquid delivered to the outlet chamber 56 during each undulation of the membrane 22. For example, the cavity dimensions (i.e., length, width, depth) determine the size of the membrane 22 that is suspended above the cavity 24, and the volume expressed in each undulation of the membrane 22 is proportional to the area of the membrane 22 and the distance the membrane 22 displaces during each undulation. The membrane 22 may displace into the cavity 24 to the full depth of the cavity, so the greater the depth of the cavity 24, the more liquid the pumping device 20 can expel in each undulation.

The pumping device 20 is configured to deliver a range of controllable and minute quantities of liquid, according to one embodiment. Because the volume of liquid expressed from the cavity 24 during each undulation of the membrane 22 is proportional to the area of the surface area of the membrane 22, the membrane is sizable to express a range of quantities of liquid. The membrane 22 may have dimensions in the range of hundreds of nanometers to hundreds of millimeters. Accordingly, the pumping device 20 may express quantities of liquid ranging from few of picoliters to hundreds of microliters with each undulation of the membrane 22.

The delivery of minutely controllable quantities of liquid enables the pumping device 20 to be useful in a variety of drug delivery applications. For example, the delivery of minute and controllable amounts of insulin to a diabetic person may help the person avoid the sharp drops in blood sugar levels that is characteristic of diabetes. As another example, the delivery of strong narcotics, such as OxyContin, Percocet, or Vicodin, in minutely controllable amounts may help patients avoid post-surgery pain while circumventing side-effects such as upset stomachs and severe itching that can be associated with taking such strong medications. Accordingly, the implementation of the pumping device 20 into drug-delivery device may be useful in a variety of applications.

Figure 5:
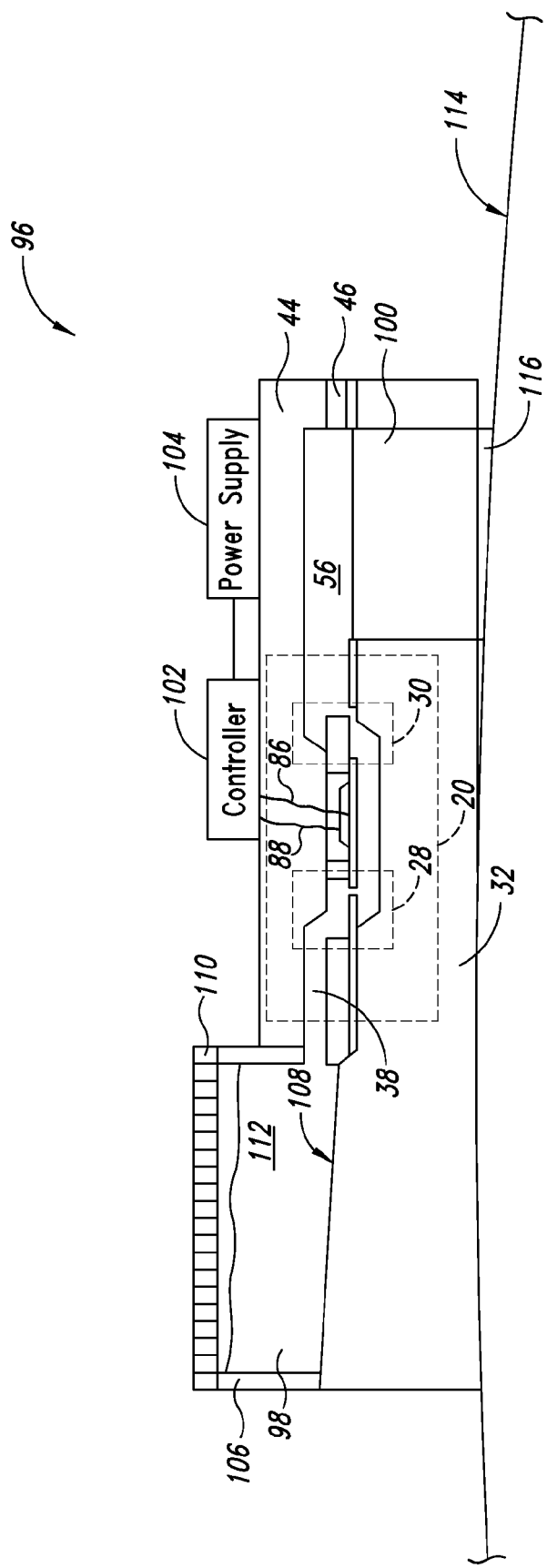
FIG. 5 is a schematic cross-sectional view illustrating a drug delivery system which incorporates the pumping device of FIGS. 1-4, according to one embodiment of the invention.

FIG. 5 is a schematic cross-sectional diagram of a drug delivery device 96, according to one embodiment of the invention. The drug delivery device 96 includes a reservoir 98, the microfluidic pumping device 20, a diffusible membrane 100, a controller 102, and a power supply 104.

The reservoir 98 is communicatively coupled to the inlet chamber 38 of the pumping device 20. The reservoir 98 includes an outer housing 106 a floor 108 and a detachable lid 110. The detachable lid 110 may be rotatably removed to insert a drug carrying agent 112. The outer housing 106 and floor 108 of the reservoir 98 contain and store the drug carrying agent 112. Because the reservoir 98 is communicatively coupled to the inlet chamber 38 the reservoir 98 supplies the pumping device 20 with the drug carrying agent 112.

The pumping device 20 may receive one or more electric field inducing voltages via traces 86 and 88 to selectively displace the membrane 22, the inlet valve member 42, and the outlet valve member 58 to selectively cause the drug carrying agent 112 to flow from the inlet chamber 38 to the outlet chamber 56.

From the outlet chamber 56, the drug carrying agent 112 flows through a drug diffusible membrane 100. The drug diffusible membrane 100 transports the drug in the agent 112 from the outlet chamber 56 to a permeable adhesive 116 for absorption by the skin 114 of a patient. The permeable adhesive 116 enables cutaneous reception of the drug through the skin 114.

The controller 102 supplies voltage signals to the pumping device 20 to selectively administer the drug contained in the drug carrying agent 112 in accordance with a routine that is selectively run by the controller 102, according to one embodiment of the invention. The controller 102 drives the pumping device 20 with a plurality of trapezoidal voltage pulses, according to one embodiment. The plurality of trapezoidal pulses have a rise time and a fall time that at least partially determine the rate of displacement of the membrane 22. According to one embodiment the fall time of each of the positive trapezoidal pulses is faster than the rise time of each of the positive trapezoidal pulses in order to cause the membrane 22 to overshoot a resting position of the membrane 22, causing a low pressure within the cavity 24 that draws additional drug carrying agent 112 past the inlet check valve 28. According to yet another embodiment, the controller 102 manipulates the frequency and magnitude of undulations by altering the rise times, fall times, duration, and amplitudes of the plurality of trapezoidal pulses. According to another embodiment, the controller 102 drives the pumping device 20 with sinusoidal, triangular, or square-wave voltage signals. The use of trapaezoidal voltage pulses is discussed in more detail in related patent application invented by Michele Palmieri, having USPTO application Ser. No. 13/294,956, and titled MICROFLUIDIC JETTING DEVICE WITH PIEZO-ELECTRIC ACTUATOR AND METHOD FOR MAKING THE SAME, which is herein cross-referenced and incorporated by reference in its entirety.

The power supply 104 delivers voltage and current to the controller 102. The power supply 104 includes a battery, such as a lithium ion battery, according to one embodiment of the invention. The battery included in the power supply 104 is interchangeable with other batteries having a similar shape, size, and power rating.

The above description of illustrated embodiments, including what is described in the Abstract, is not intended to be exhaustive or to limit the embodiments to the precise forms disclosed. Although specific embodiments and examples are described herein for illustrative purposes, various equivalent modifications can be made without departing from the spirit and scope of the disclosure, as will be recognized by those skilled in the relevant art.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety, including: U.S. Pat. Nos. 6,294,860; 6,673,593; 6,693,039; 6,770,471; 7,678,600; 7,705,416; 7,754,578; and 7,811,848 in addition to foreign publications JP2003133604 and JP10287268. Aspects of the embodiments can be modified, if necessary to employ concepts of the various patents, applications and publications to provide yet further embodiments.

I claim:

1. A liquid displacement apparatus, comprising:
   a silicon substrate;
   a first cavity formed in the substrate and having an inlet side and an outlet side;
   a piezoelectrically displaceable membrane positioned above the first cavity at least partially enclosing the cavity;
   a ceiling member positioned above the membrane;
   a second cavity positioned proximate the inlet side of the first cavity; and
   an inlet valve member at least partially suspended above the first cavity, the inlet valve member communicatively couples the second cavity to the first cavity by swinging to a first position that is at least partially in the first cavity in response to displacement of the membrane to a first displacement position and communicatively decouples the first cavity from the second cavity by swinging to a second position that is at least partially in the second cavity;
   a third cavity formed proximate to the outlet side of the first cavity and having an upper portion bound by the ceiling member and a lower portion bound by the substrate; and
   an outlet valve member positioned between the first cavity and the third cavity, the outlet valve member at least partially suspended over the first cavity and extending from the membrane, wherein the outlet valve member communicatively couples and decouples the first cavity to the third cavity by flexibly swinging between a third position that is at least partially in the third cavity and a fourth position that is at least partially in the first cavity, the outlet valve member abutting the substrate in the fourth position and communicatively decoupling the third cavity from the first cavity in response to displacement of the membrane to the first displacement position when in the fourth position.

2. The apparatus of claim 1 wherein the inlet valve member communicatively decouples the first cavity from the second cavity in response to displacement of the membrane to a second displacement position different from the first displacement position.

3. The apparatus of claim 1 wherein the outlet valve member flexibly swings to the fourth position in the first cavity and the inlet valve member flexibly swings to the first position in the first cavity in response to displacement of the membrane to the first displacement position, and the outlet valve member flexibly swings to the third position in the third cavity and the inlet valve member flexibly swings to the second position in the second cavity in response to displacement of the membrane to a second displacement position different from the first displacement position.

4. The apparatus of claim 1 wherein the second cavity includes an upper portion bound by the ceiling member and a lower portion bound by the substrate.

5. The apparatus of claim 1 wherein the inlet valve member extends from the substrate.

6. A liquid displacement apparatus comprising:
   a silicon substrate;
   a first cavity formed in the substrate and having an inlet side and an outlet side;
   a piezoelectrically displaceable membrane positioned above the first cavity at least partially enclosing the cavity;
   a ceiling member positioned above the membrane;
   a second cavity positioned proximate the inlet side of the first cavity; and
   an inlet valve member at least partially suspended above the first cavity, the inlet valve member communicatively couples the second cavity to the first cavity by swinging to a first position that is at least partially in the first cavity in response to displacement of the membrane to a first displacement position and communicatively decouples the first cavity from the second cavity by swinging to a second position that is at least partially in the second cavity;
   a third cavity formed proximate to the outlet side of the first cavity and having an upper portion bound by the ceiling member and a lower portion bound by the substrate; and
   an outlet valve member positioned between the first cavity and the third cavity, the outlet valve member at least partially suspended over the cavity and extending from the membrane, wherein the outlet valve member communicatively couples and decouples the first cavity to the third cavity by flexibly swinging between a third position that is at least partially in the third cavity and a fourth position that is at least partially in the first cavity, wherein the inlet valve member communicatively decouples the first cavity from the second cavity in response to displacement of the membrane to a second displacement position different from the first displacement position and the inlet valve member abuts the ceiling member in the second position thereby communicatively decoupling the first cavity from the second cavity.

7. The apparatus of claim 6 wherein the outlet valve member abuts the substrate in the fourth position thereby communicatively decoupling the third cavity from the first cavity in response to displacement of the membrane to the first displacement position.

8. A drug delivery device, comprising:
   a portable power supply;
   a drug reservoir; and
   a liquid displacement apparatus, including:
      a silicon substrate,
      a cavity formed in the substrate,
      a piezoelectrically displaceable membrane positioned above the cavity to at least partially enclose the cavity,
      a ceiling member positioned above the membrane, and
      an inlet valve member partially suspended above the cavity and configured to communicatively couple the drug reservoir to the cavity by swinging to a first position having part of the inlet valve member in the cavity and to communicatively decouple the cavity from the drug reservoir by swinging to a second position having part of the inlet valve member in the inlet chamber in response to displacements of the membrane;
      an outlet chamber;
      an outlet valve member extending from the membrane and configured to couple and decouple the outlet chamber from the cavity by swinging between a third position having part of the outlet valve member in the outlet chamber and a fourth position having part of the outlet valve member in the cavity in response to displacements of the membrane, the outlet valve member being a second check valve, that abuts the substrate when in the fourth position to stop a backflow of drug from the outlet chamber to the cavity.

9. A method of moving liquid, comprising:

displacing a piezoelectrically actuated membrane, suspended above a cavity formed in a silicon substrate, between a first position that is proximate the cavity relative to a resting position of the membrane and a second position that is away from the cavity relative to the resting position of the membrane;

communicatively decoupling an inlet chamber and the cavity by swinging a free end of an inlet cantilever into the inlet chamber and communicatively coupling the inlet chamber and the cavity by swinging the free end of the inlet cantilever into the cavity in response to displacing the piezoelectrically actuated membrane; and communicatively coupling an outlet chamber and the cavity by swinging a free end of an outlet cantilever into an outlet chamber and communicatively decoupling the outlet chamber and the cavity by swinging the free end of the outlet cantilever into the cavity to abut the substrate in the fourth position by displacing the piezoelectrically actuated membrane.

10. The method of claim 9, further comprising:

inhibiting flow of a fluid from the cavity to the inlet chamber by communicatively decoupling the cavity from the inlet chamber in response to displacing the membrane towards the first position.

11. The method of claim 10, further comprising:

allowing flow of the fluid from the cavity to the outlet chamber by communicatively coupling the cavity to the outlet chamber in response to displacing the membrane towards the first position.

12. The method of claim 9, further comprising:

inhibiting flow of a fluid from the outlet chamber to the cavity by communicatively decoupling the cavity from the outlet chamber in response to displacing the membrane towards the second position.

13. The method of claim 12, further comprising:

allowing flow of the fluid from the inlet chamber to the cavity by communicatively coupling the cavity to the inlet chamber in response to displacing the membrane towards the second position.

* * * * *